(12) United States Patent
Leven

(10) Patent No.: US 9,180,291 B2
(45) Date of Patent: Nov. 10, 2015

(54) SIDE LOAD LEAD ANCHOR AND METHODS AND SYSTEMS USING THE LEAD ANCHOR

(71) Applicant: BOSTON SCIENTIFIC NEUROMODULATION CORPORATION, Valencia, CA (US)

(72) Inventor: Jacob B. Leven, Huntington Beach, CA (US)

(73) Assignee: Boston Scientific Neuromodulation Corporation, Valencia, CA (US)

( * ) Notice: Subject to any disclaimer, the term of this patent is extended or adjusted under 35 U.S.C. 154(b) by 0 days.

(21) Appl. No.: 14/325,197

(22) Filed: Jul. 7, 2014

(65) Prior Publication Data

US 2015/0018914 A1 Jan. 15, 2015

Related U.S. Application Data

(60) Provisional application No. 61/844,590, filed on Jul. 10, 2013.

(51) Int. Cl.
*A61N 1/00* (2006.01)
*A61N 1/05* (2006.01)
(52) U.S. Cl.
CPC ............ *A61N 1/0558* (2013.01); *A61N 1/0553* (2013.01)
(58) Field of Classification Search
CPC ........... C12Q 1/6827; C12Q 2565/125; C12Q 2565/501; A61N 1/0553; A61N 1/0558
See application file for complete search history.

(56) References Cited

U.S. PATENT DOCUMENTS

| | | | |
|---|---|---|---|
| 6,181,969 B1 | 1/2001 | Gord | |
| 6,516,227 B1 | 2/2003 | Meadows et al. | |
| 6,609,029 B1 | 8/2003 | Mann et al. | |
| 6,609,032 B1 | 8/2003 | Woods et al. | |
| 6,741,892 B1 | 5/2004 | Meadows et al. | |
| 7,244,150 B1 | 7/2007 | Brase et al. | |
| 7,437,193 B2 | 10/2008 | Parramon et al. | |
| 7,672,734 B2 | 3/2010 | Anderson et al. | |
| 7,761,165 B1 | 7/2010 | He et al. | |
| 7,949,395 B2 | 5/2011 | Kuzma | |
| 7,974,706 B2 | 7/2011 | Moffitt et al. | |
| 8,175,710 B2 | 5/2012 | He | |
| 8,224,450 B2 | 7/2012 | Brase | |
| 8,364,278 B2 | 1/2013 | Pianca et al. | |
| 2007/0150036 A1 | 6/2007 | Anderson | |
| 2012/0035692 A1* | 2/2012 | Cantlon et al. | 607/116 |

\* cited by examiner

*Primary Examiner* — George Manuel
(74) *Attorney, Agent, or Firm* — Lowe Graham Jones PLLC; Bruce E. Black

(57) ABSTRACT

A lead anchor includes an anchor body defining an open lead channel; and a rotatable locking element shaped as a portion of a ring and defining a central cavity, an entrance slit, and a protruding nodule extending into the central cavity. The anchor body further defines a locking element channel arranged perpendicular to the lead channel to receive the rotatable locking element. In an open position, the entrance slit of the locking element is aligned with the lead channel of the anchor body so that a lead can be loaded into the lead channel and, in a closed position, the entrance slit is not aligned with the lead channel to prevent a lead disposed in the lead channel from disengaging from the lead anchor. In the closed position, the nodule on the locking element engages the lead and resists rotation of the locking element to the open position.

20 Claims, 9 Drawing Sheets

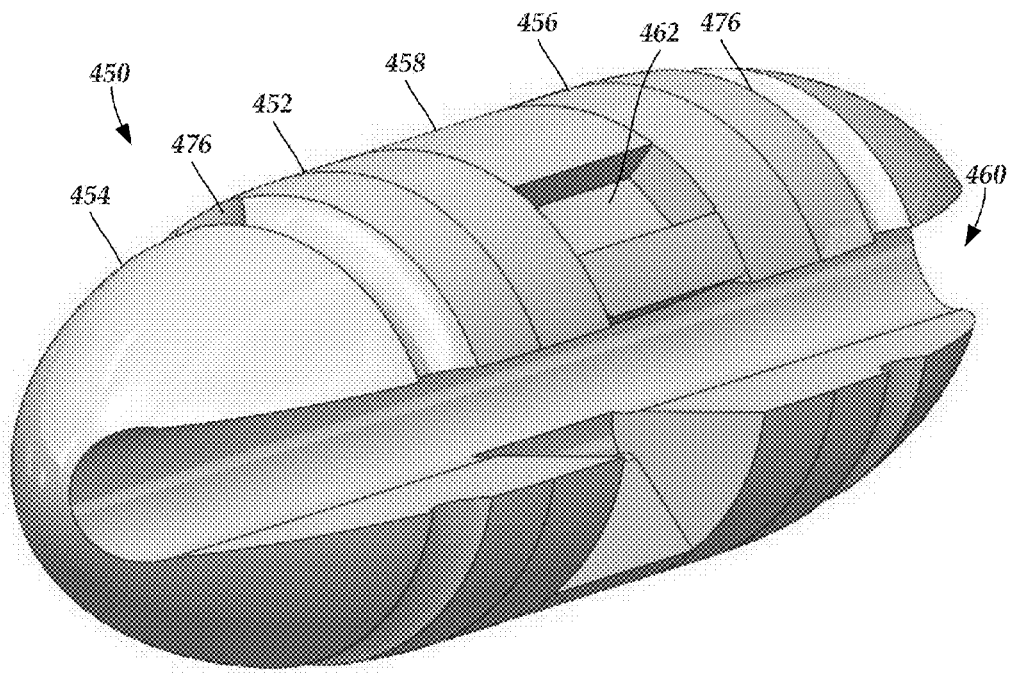
Figure 4A
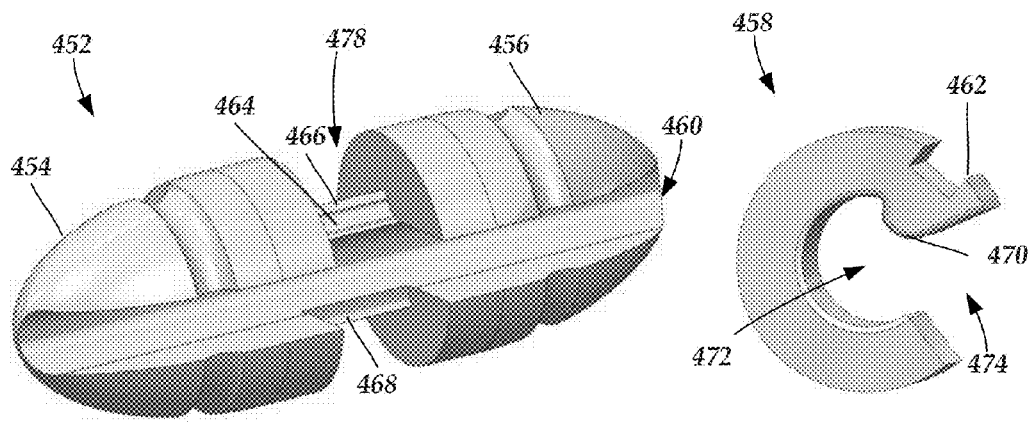 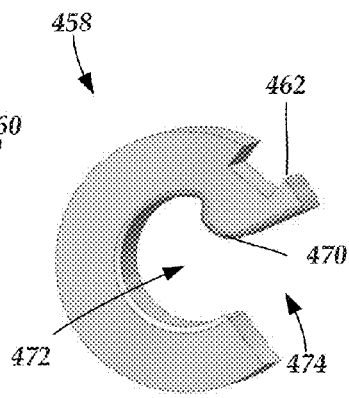
Figure 4B                    Figure 4C

SIDE LOAD LEAD ANCHOR AND METHODS AND SYSTEMS USING THE LEAD ANCHOR

CROSS-REFERENCE TO RELATED APPLICATIONS

This application claims the benefit under 35 U.S.C. §119 (e) of U.S. Provisional Patent Application Ser. No. 61/844,590, filed Jul. 10, 2013, which is incorporated herein by reference.

FIELD

The present invention is directed to the area of implantable electrical stimulation systems and methods of making and using the systems. The present invention is also directed implantable electrical stimulation leads having a lead anchor as well as methods of making and using the leads and electrical stimulation systems.

BACKGROUND

Implantable electrical stimulation systems have proven therapeutic in treating a variety of diseases, injuries, and disorders. For example, spinal cord stimulation systems have been used as a therapeutic modality for the treatment of chronic pain syndromes. Peripheral nerve stimulation has been used to treat chronic pain syndrome and incontinence, with a number of other applications under investigation. Functional electrical stimulation systems have been applied to restore some functionality to paralyzed extremities in spinal cord injury patients.

Stimulators have been developed to provide therapy for a variety of treatments. A stimulator can include a control module (with a pulse generator), one or more leads, and an array of stimulator electrodes on each lead. The stimulator electrodes are in contact with or near the nerves, muscles, or other tissue to be stimulated. The pulse generator in the control module generates electrical pulses that are delivered by the electrodes to body tissue.

BRIEF SUMMARY

One embodiment is a lead anchor including an anchor body having a proximal end and a distal end and defining an open lead channel extending longitudinally from the proximal end to the distal end; and a rotatable locking element shaped as a portion of a ring and defining a central cavity and an entrance slit. The locking element further defines a protruding nodule extending into the central cavity. The anchor body further defines a locking element channel arranged perpendicular to the lead channel to receive the rotatable locking element and to permit rotation of the locking element from an open position to a closed position. In the open position, the entrance slit of the locking element is aligned with the lead channel of the anchor body so that a lead can be loaded into the lead channel and, in the closed position, the entrance slit is not aligned with the lead channel to prevent a lead disposed in the lead channel from disengaging from the lead anchor. When a lead is in the lead channel and the locking element is in the closed position, the nodule on the locking element engages the lead and resists rotation of the locking element to the open position.

Another embodiment is a kit including a lead and the lead anchor described above.

A further embodiment is a method of implanting a lead. The method includes inserting a portion of a lead into an open lead channel of the lead anchor described above with the locking element in the open position; and rotating the locking element of the lead anchor to the closed position to lock the lead within the lead anchor. In the closed position, the nodule on the locking element engages the lead and resists rotation of the locking element to the open position and the entrance slit of the locking element is not aligned with the lead channel to prevent the lead disposed in the lead channel from disengaging from the lead anchor.

BRIEF DESCRIPTION OF THE DRAWINGS

Non-limiting and non-exhaustive embodiments of the present invention are described with reference to the following drawings. In the drawings, like reference numerals refer to like parts throughout the various figures unless otherwise specified.

For a better understanding of the present invention, reference will be made to the following Detailed Description, which is to be read in association with the accompanying drawings, wherein:

FIG. 4A is a schematic perspective view of one embodiment of a lead anchor, according to the invention;

FIG. 4B is a schematic perspective view of the anchor body of the lead anchor of FIG. 4A, according to the invention;

FIG. 4C is a schematic perspective view of the rotatable locking element of the lead anchor of FIG. 4A, according to the invention;

DETAILED DESCRIPTION

The present invention is directed to the area of implantable electrical stimulation systems and methods of making and using the systems. The present invention is also directed implantable electrical stimulation leads having a lead anchor as well as methods of making and using the leads and electrical stimulation systems.

Suitable implantable electrical stimulation systems include, but are not limited to, a least one lead with one or more electrodes disposed along a distal end of the lead and one or more terminals disposed along the one or more proximal ends of the lead. Leads include, for example, percutaneous leads, paddle leads, and cuff leads. Examples of electrical stimulation systems with leads are found in, for example, U.S. Pat. Nos. 6,181,969; 6,516,227; 6,609,029; 6,609,032; 6,741,892; 7,949,395; 7,244,150; 7,672,734; 7,761,165; 7,974,706; 8,175,710; 8,224,450; and 8,364,278; and U.S. Patent Application Publication No. 2007/0150036, all of which are incorporated by reference.

Figure 1:
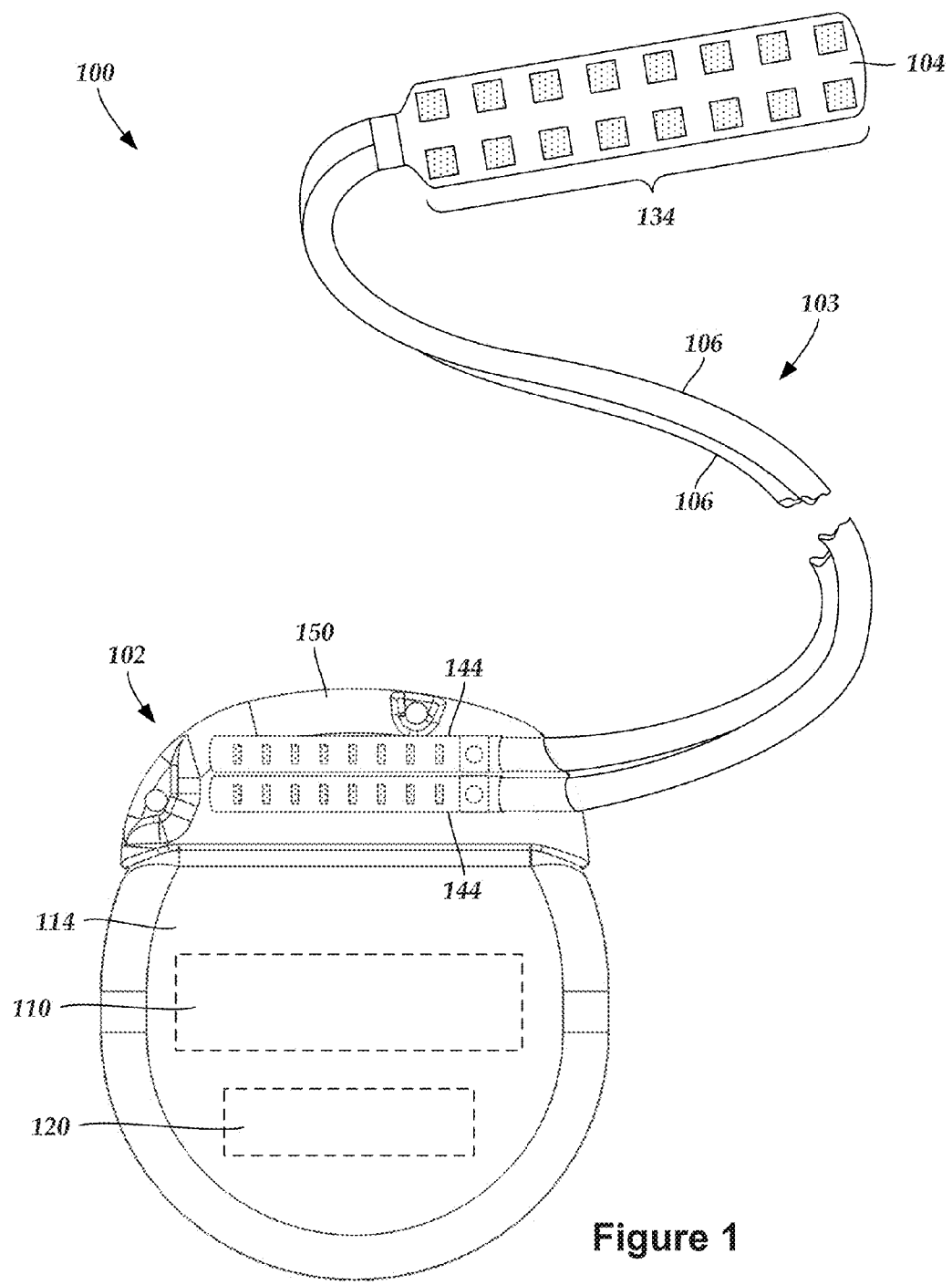
FIG. 1 is a schematic side view of one embodiment of an electrical stimulation system that includes a paddle lead electrically coupled to a control module, according to the invention.

FIG. 1 illustrates schematically one embodiment of an electrical stimulation system 100. The electrical stimulation system includes a control module (e.g., a stimulator or pulse generator) 102 and a lead 103 coupleable to the control module 102. The lead 103 includes a paddle body 104 and one or more lead bodies 106. In FIG. 1, the lead 103 is shown having two lead bodies 106. It will be understood that the lead 103 can include any suitable number of lead bodies including, for example, one, two, three, four, five, six, seven, eight or more lead bodies 106. An array of electrodes 133, such as electrode 134, is disposed on the paddle body 104, and an array of terminals (e.g., 210 in FIG. 2A-2B) is disposed along each of the one or more lead bodies 106.

It will be understood that the electrical stimulation system can include more, fewer, or different components and can have a variety of different configurations including those configurations disclosed in the electrical stimulation system references cited herein. For example, instead of a paddle body, the electrodes can be disposed in an array at or near the distal end of a lead body forming a percutaneous lead.

Figure 2:
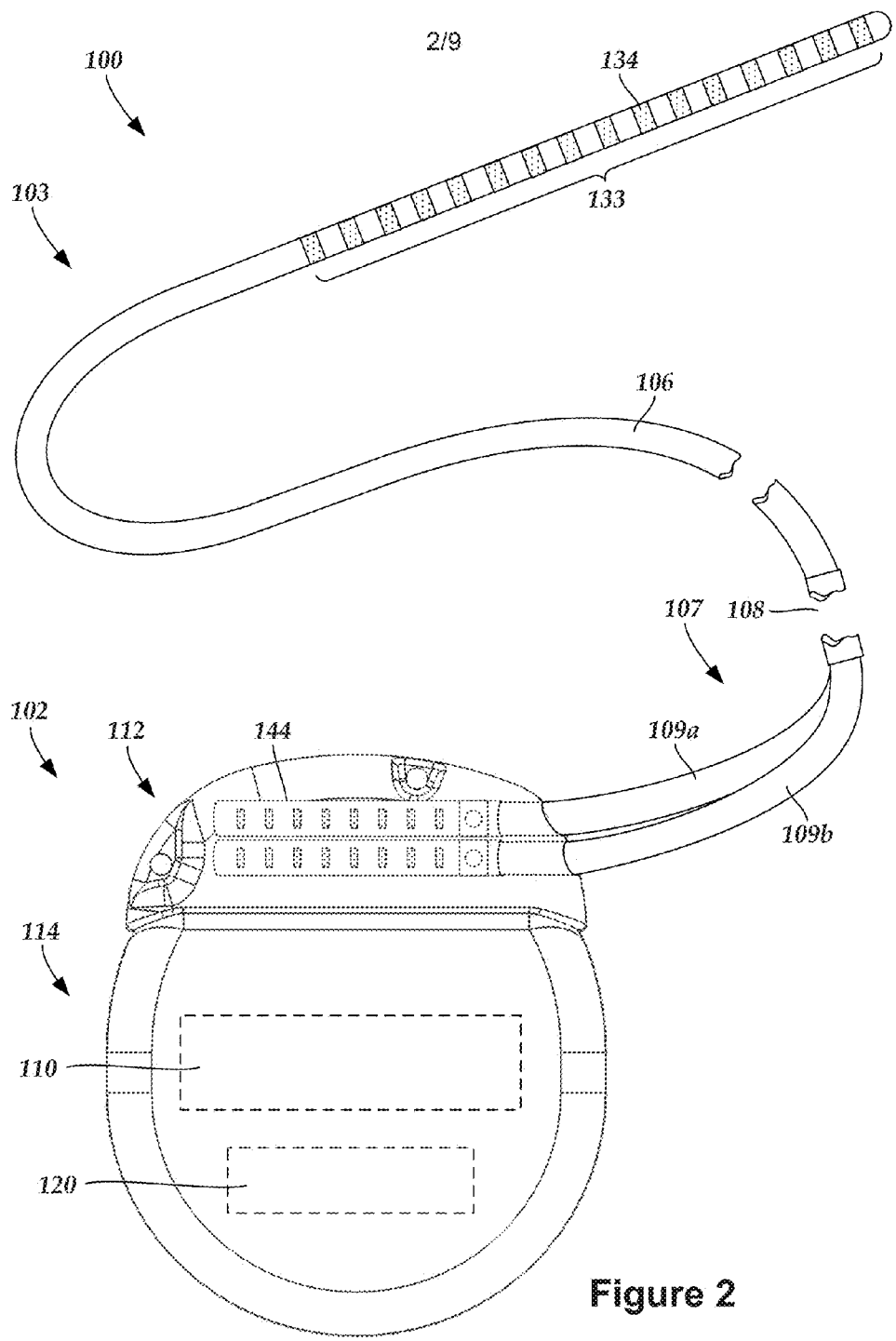
FIG. 2 is a schematic side view of one embodiment of an electrical stimulation system that includes a percutaneous lead electrically coupled to a control module, according to the invention.

FIG. 2 illustrates schematically another embodiment of the electrical stimulation system 100, where the lead 103 is a percutaneous lead. In FIG. 2, the electrodes 134 are shown disposed along the one or more lead bodies 106. In at least some embodiments, the lead 103 is isodiametric along a longitudinal length of the lead body 106.

The lead 103 can be coupled to the control module 102 in any suitable manner. In FIG. 1, the lead 103 is shown coupling directly to the control module 102. In at least some other embodiments, the lead 103 couples to the control module 102 via one or more intermediate devices (300 in FIGS. 3A-3B). For example, in at least some embodiments one or more lead extensions 324 (see e.g., FIG. 3B) can be disposed between the lead 103 and the control module 102 to extend the distance between the lead 103 and the control module 102. Other intermediate devices may be used in addition to, or in lieu of, one or more lead extensions including, for example, a splitter, an adaptor, or the like or combinations thereof. It will be understood that, in the case where the electrical stimulation system 100 includes multiple elongated devices disposed between the lead 103 and the control module 102, the intermediate devices may be configured into any suitable arrangement.

In FIG. 2, the electrical stimulation system 100 is shown having a splitter 207 configured and arranged for facilitating coupling of the lead 103 to the control module 102. The splitter 207 includes a splitter connector 208 configured to couple to a proximal end of the lead 103, and one or more splitter tails 209a and 209b configured and arranged to couple to the control module 102 (or another splitter, a lead extension, an adaptor, or the like).

The control module 102 typically includes a connector housing 112 and a sealed electronics housing 114. An electronic subassembly 110 and an optional power source 120 are disposed in the electronics housing 114. A control module connector 144 is disposed in the connector housing 112. The control module connector 144 is configured and arranged to make an electrical connection between the lead 103 and the electronic subassembly 110 of the control module 102.

The electrical stimulation system or components of the electrical stimulation system, including the paddle body 104, the one or more of the lead bodies 106, and the control module 102, are typically implanted into the body of a patient. The electrical stimulation system can be used for a variety of applications including, but not limited to deep brain stimulation, neural stimulation, spinal cord stimulation, muscle stimulation, and the like.

The electrodes 134 can be formed using any conductive, biocompatible material. Examples of suitable materials include metals, alloys, conductive polymers, conductive carbon, and the like, as well as combinations thereof. In at least some embodiments, one or more of the electrodes 134 are formed from one or more of: platinum, platinum iridium, palladium, palladium rhodium, or titanium.

Any suitable number of electrodes 134 can be disposed on the lead including, for example, four, five, six, seven, eight, nine, ten, eleven, twelve, fourteen, sixteen, twenty-four, thirty-two, or more electrodes 134. In the case of paddle leads, the electrodes 134 can be disposed on the paddle body 104 in any suitable arrangement. In FIG. 1, the electrodes 134 are arranged into two columns, where each column has eight electrodes 134.

The electrodes of the paddle body 104 (or one or more lead bodies 106) are typically disposed in, or separated by, a non-conductive, biocompatible material such as, for example, silicone, polyurethane, polyetheretherketone ("PEEK"), epoxy, and the like or combinations thereof. The one or more lead bodies 106 and, if applicable, the paddle body 104 may be formed in the desired shape by any process including, for example, molding (including injection molding), casting, and the like. The non-conductive material typically extends from the distal ends of the one or more lead bodies 106 to the proximal end of each of the one or more lead bodies 106.

In the case of paddle leads, the non-conductive material typically extends from the paddle body 104 to the proximal end of each of the one or more lead bodies 106. Additionally, the non-conductive, biocompatible material of the paddle body 104 and the one or more lead bodies 106 may be the same or different. Moreover, the paddle body 104 and the one or more lead bodies 106 may be a unitary structure or can be formed as two separate structures that are permanently or detachably coupled together.

Figure 3A:
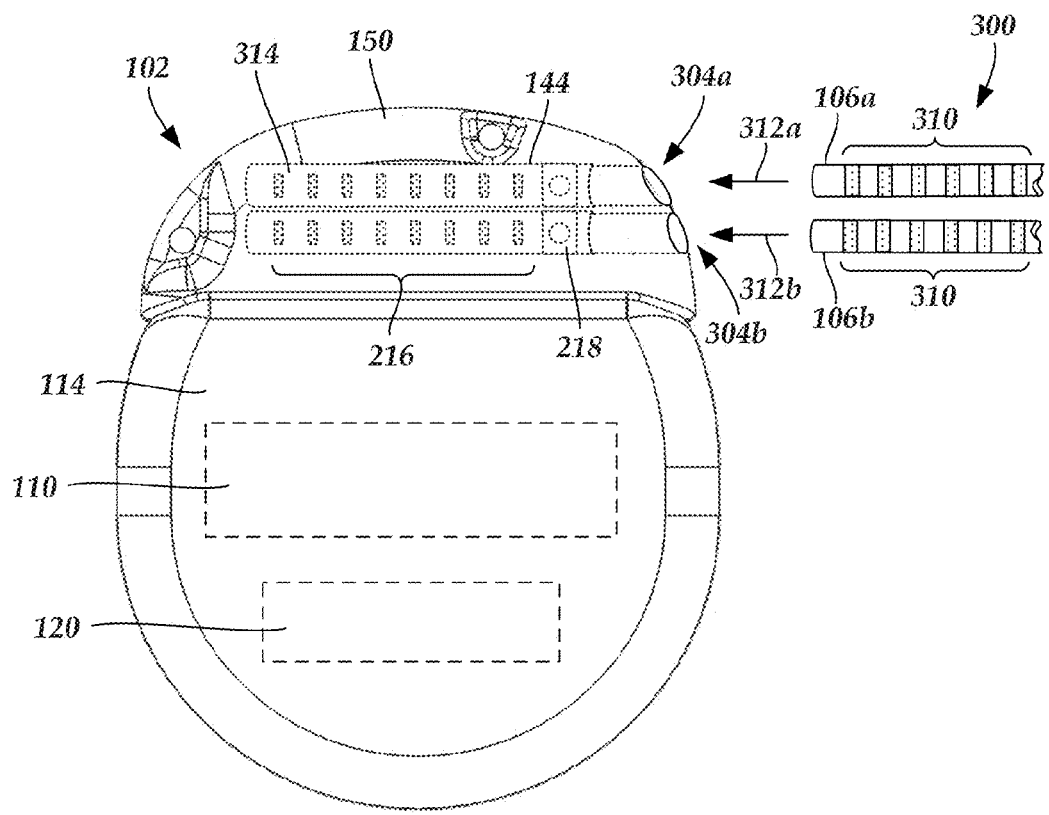
FIG. 3A is a schematic side view of one embodiment of the control module of FIG. 1 configured and arranged to electrically couple to an elongated device, according to the invention.
Figure 3B:
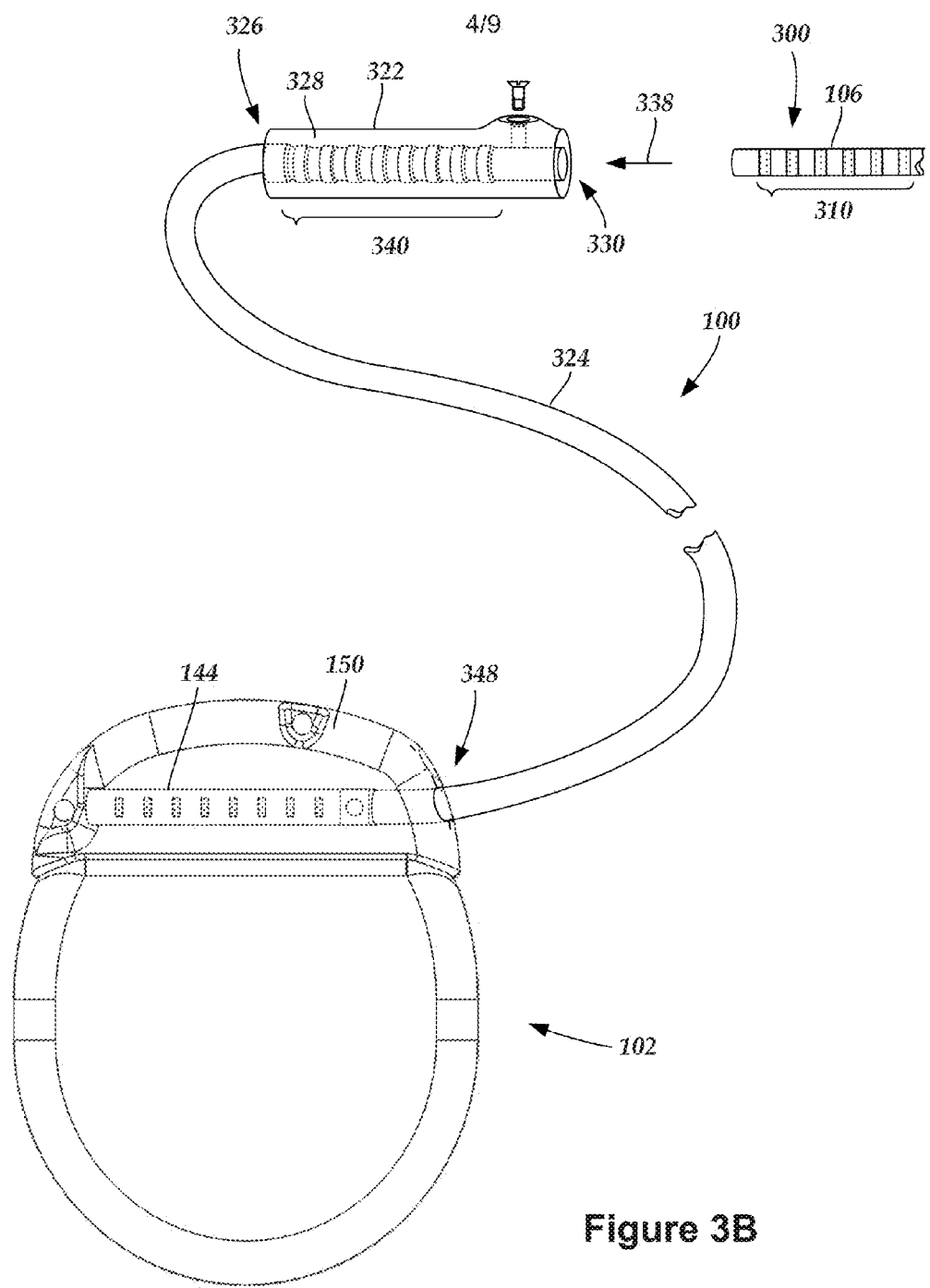
FIG. 3B is a schematic side view of one embodiment of a lead extension configured and arranged to electrically couple the elongated device of FIG. 2 to the control module of FIG. 1, according to the invention.

Terminals (e.g., 310 in FIGS. 3A-3B) are typically disposed along the proximal end of the one or more lead bodies 106 of the electrical stimulation system 100 (as well as any splitters, lead extensions, adaptors, or the like) for electrical connection to corresponding connector contacts (e.g., 314 in FIGS. 3A-3B). The connector contacts are disposed in connectors (e.g., 144 in FIGS. 1-3B; and 322 FIG. 3B) which, in turn, are disposed on, for example, the control module 102 (or a lead extension, a splitter, an adaptor, or the like). Electrically conductive wires, cables, or the like (not shown) extend from the terminals to the electrodes 134. Typically, one or more electrodes 134 are electrically coupled to each terminal. In at least some embodiments, each terminal is only connected to one electrode 134.

The electrically conductive wires ("conductors") may be embedded in the non-conductive material of the lead body 106 or can be disposed in one or more lumens (not shown) extending along the lead body 106. In some embodiments, there is an individual lumen for each conductor. In other embodiments, two or more conductors extend through a lumen. There may also be one or more lumens (not shown) that open at, or near, the proximal end of the one or more lead bodies 106, for example, for inserting a stylet to facilitate placement of the one or more lead bodies 106 within a body of a patient. Additionally, there may be one or more lumens (not shown) that open at, or near, the distal end of the one or more lead bodies 106, for example, for infusion of drugs or medication into the site of implantation of the one or more lead bodies 106. In at least one embodiment, the one or more lumens are flushed continually, or on a regular basis, with saline, epidural fluid, or the like. In at least some embodiments, the one or more lumens are permanently or removably sealable at the distal end.

FIG. 3A is a schematic side view of one embodiment of a proximal end of one or more elongated devices 300 configured and arranged for coupling to one embodiment of the control module connector 144. The one or more elongated devices may include, for example, one or more of the lead bodies 106 of FIG. 1, one or more intermediate devices (e.g., a splitter, the lead extension 324 of FIG. 3B, an adaptor, or the like or combinations thereof), or a combination thereof.

The control module connector 144 defines at least one port into which a proximal end of the elongated device 300 can be inserted, as shown by directional arrows 312a and 312b. In FIG. 3A (and in other figures), the connector housing 112 is shown having two ports 304a and 304b. The connector housing 112 can define any suitable number of ports including, for example, one, two, three, four, five, six, seven, eight, or more ports.

The control module connector 144 also includes a plurality of connector contacts, such as connector contact 314, disposed within each port 304a and 304b. When the elongated device 300 is inserted into the ports 304a and 304b, the connector contacts 314 can be aligned with a plurality of terminals 310 disposed along the proximal end(s) of the elongated device(s) 300 to electrically couple the control module 102 to the electrodes (134 of FIG. 1) disposed on the paddle body 104 of the lead 103. Examples of connectors in control modules are found in, for example, U.S. Pat. Nos. 7,244,150 and 8,224,450, which are incorporated by reference.

FIG. 3B is a schematic side view of another embodiment of the electrical stimulation system 100. The electrical stimulation system 100 includes a lead extension 324 that is configured and arranged to couple one or more elongated devices 300 (e.g., one of the lead bodies 106 of FIGS. 1 and 2, the splitter 207 of FIG. 2, an adaptor, another lead extension, or the like or combinations thereof) to the control module 102. In FIG. 3B, the lead extension 324 is shown coupled to a single port 304 defined in the control module connector 144. Additionally, the lead extension 324 is shown configured and arranged to couple to a single elongated device 300. In alternate embodiments, the lead extension 324 is configured and arranged to couple to multiple ports 304 defined in the control module connector 144, or to receive multiple elongated devices 300, or both.

A lead extension connector 322 is disposed on the lead extension 324. In FIG. 3B, the lead extension connector 322 is shown disposed at a distal end 326 of the lead extension 324. The lead extension connector 322 includes a connector housing 328. The connector housing 328 defines at least one port 330 into which terminals 310 of the elongated device 300 can be inserted, as shown by directional arrow 338. The connector housing 328 also includes a plurality of connector contacts, such as connector contact 340. When the elongated device 300 is inserted into the port 330, the connector contacts 240 disposed in the connector housing 328 can be aligned with the terminals 310 of the elongated device 300 to electrically couple the lead extension 324 to the electrodes (134 of FIGS. 1 and 2) disposed along the lead (103 in FIGS. 1 and 2).

In at least some embodiments, the proximal end of the lead extension 324 is similarly configured and arranged as a proximal end of the lead 103 (or other elongated device 300). The lead extension 324 may include a plurality of electrically conductive wires (not shown) that electrically couple the connector contacts 340 to a proximal end 348 of the lead extension 324 that is opposite to the distal end 326. In at least some embodiments, the conductive wires disposed in the lead extension 324 can be electrically coupled to a plurality of terminals (not shown) disposed along the proximal end 348 of the lead extension 324. In at least some embodiments, the proximal end 348 of the lead extension 324 is configured and arranged for insertion into a connector disposed in another lead extension (or another intermediate device). In other embodiments (and as shown in FIG. 3B), the proximal end 348 of the lead extension 324 is configured and arranged for insertion into the control module connector 144.

A lead can be anchored in patient tissue using a lead anchor. More particularly, a lead anchor can be designed so that the lead is side loaded into the lead anchor in contrast to many conventional lead anchors that are slid onto the lead starting at either the proximal or distal end of the lead. This is particular advantageous for leads that are not isodiametric or which are birfurcated or branched. In such lead, it may be difficult to slide a lead anchor along the lead. The lead anchors disclosed herein permit side loading of a lead into a lead channel and then the lead anchor is closed by the rotation of a clasp whose axis of rotation is offset from the primary axis of the lead.

FIG. 4A illustrates one embodiment of a lead anchor 450 that includes an anchor body 452 having a proximal end and a distal end and an open lead channel 460 extending longitudinally along the entire anchor body 452 from its proximal end to the distal end. The lead channel 460 may be defined as a cylindrical groove having a circular cross section. Alternatively, the open lead channel 460 may have a triangular, rectangular, or polygonal cross section that may also vary depending on the shape or size of the lead to be received in the lead channel. The lead anchor and its lead channel 460 lateral loading (i.e., side loading) of the lead into the lead anchor 450.

The anchor body 452 can include a first portion 454 and a second portion 456. The first portion 454 and the second portion may or may not be identical in shape or size (such as, length and diameter) to each other. Further, the first portion 454 and the second portion 456 may vary in shape or size based on the anatomy of the patient.

The lead anchor 450 also includes a rotatable locking element 458 disposed between the first portion 454 and the second portion 456. The locking element 458 is described in detail with respect to FIGS. 4B-4C.

The anchor body 452 optionally includes at least one suture channel 476 formed in the outer surface of the anchor body 452. The suture channel 476 cane receiving a suture that extends around the lead anchor 450 to fix the lead anchor to patient tissue.

FIG. 4B illustrates one embodiment of the anchor body 452 with the rotatable locking element 458 (see, FIG. 4C) removed. An axle 464 connects the first portion 454 of the anchor body 452 to the second portion 456 of the anchor body. The axle 464 may be shaped as an arc partially extending with an angle less than 360 degrees along the longitudinal axis of the lead anchor 450.

The axle 464 may further define at least one end stop. Each end stop is provided to stop or hinder rotation of the rotatable locking element 458 beyond the end stop. In at least some embodiments, a first end stop 466 and a second end stop 468 may be positioned on the axle 464. Alternatively, one or both of the first end stop and the second end stop may be formed as extensions from the surface of the first portion 454 or the second portion 456 (of both) of the anchor body 452. Further, the first end stop 466 and the second end stop 468 may form a unitary structure with the axle 464 or the surface of the first portion 454 or the second portion 456. Each of the first and second end stops 466-468 of the axle 464 may interact with a nodule 470 (or any other portion of) the locking element 458 (see, FIG. 4C) to prevent or hinder further rotation of the locking element 458 in one direction. In one embodiment, the first end stop 466 resists further rotation of the rotatable locking element 458 in a clockwise direction and the second end stop 468 resists further rotation of the rotatable locking element 458 in a counterclockwise direction.

In at least some embodiments, the rotatable locking element 458 rests on the axle 464. The anchor body 452 defines a locking element channel 478 that may be arranged perpendicular to the lead channel 460. The locking element channel 478 receives the rotatable locking element 458. Further, the locking element channel 478 permits rotation of the rotatable locking element 458 from an open position to a closed position.

FIG. 4C illustrates one embodiment of the rotatable locking element 458 of the lead anchor 450. The rotatable locking element 458 may be shaped as a portion of a ring. The rotatable locking element 458 defines a central cavity 472 and an entrance slit 474. The entrance slit 474, when aligned with the leach channel 450, allows the lead (see 403 in FIG. 5A) to be loaded into the lead channel 460. The entrance slit 474 may also be useful for coupling the rotatable locking element 458 to the axle 464 of the anchor body 452. The central cavity 472 is dimensioned so that the rotatable locking element 458 can rest on the axle 464 and allow rotational movement of the locking element 458. In at least some embodiments, the rotatable locking element 458 is a C shaped swivel (c-swivel).

The rotatable locking element 458 preferably includes an indentation 462, or other element such as a projection, formed in an outer (i.e., peripheral) surface thereof to facilitate rotation of the locking element 458 by a user to and from the locking position. The indentation 462 may be a finger grip portion to allow the user to hold, grip, or otherwise move the locking element 458 conveniently to rotate the locking element 458.

In at least some embodiments, the rotatable locking element 458 further defines a protruding nodule 470 that extends into the central cavity 472. During use, the nodule 470 can impinge on a lead (such as the lead 403) within the lead channel so as to secure the lead into the lead anchor 450. Though the nodule 470 is shown to have a C-shape, it will be understood that the nodule 470 may have any suitable structure or shape, such as, but not limited to, an arcuate shape, a flat surface, and the like.

Figure 5A:
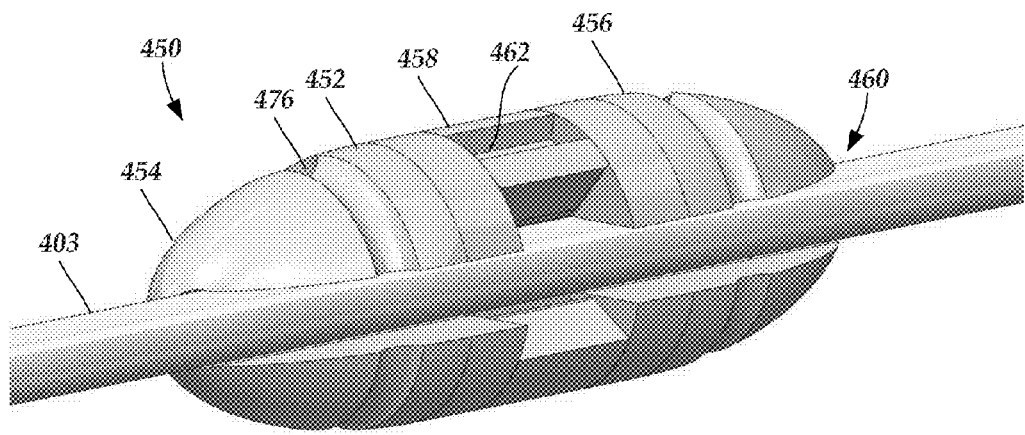
FIG. 5A is a schematic perspective view of the lead anchor of FIG. 4A in the open position, according to the invention.

FIG. 5A illustrates the lead anchor 450 in the open or load position. As shown, a lead 403 can be loaded laterally (i.e., side loaded) into the lead channel 460 of the lead anchor 450. When the locking element 458 is in the open position or the unlocked state, the entrance slit 474 of the locking element 458 is aligned with the lead channel 460 of the anchor body 452 so that the lead 403 can be loaded into the lead channel 460.

Figure 5B:
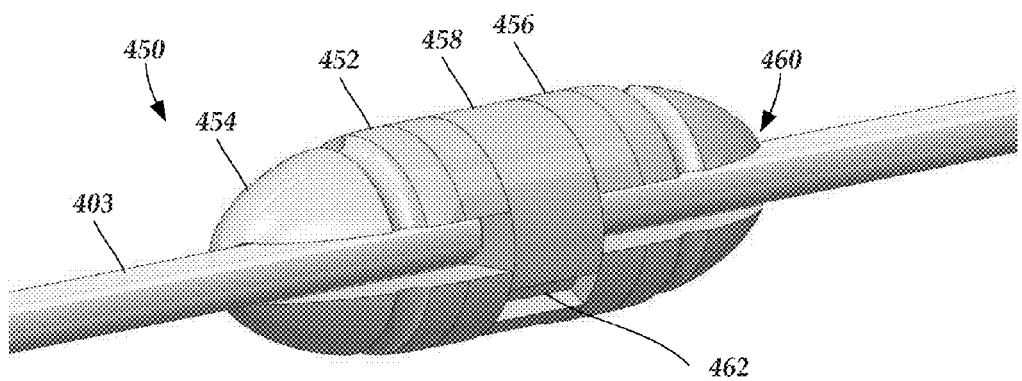
FIG. 5B is a schematic perspective view of the lead anchor of FIG. 4A in the closed position, according to the invention.

FIG. 5B illustrates the lead anchor 450 of FIG. 4A in the closed or locked position. As shown, when the locking element 458 is in the closed position, the entrance slit 474 is not aligned with the lead channel 460 which prevents the lead 403 disposed in the lead channel 460 from disengaging from the lead anchor 450. In addition, when the lead 403 is in the lead channel 460 and the rotatable locking element 458 is in the closed or locked position, the nodule 470 on the locking element 458 may engage the lead 403 and to resist rotation of the locking element 458 to the open position. In at least some embodiments, when the lead anchor 450 is in the closed position, the nodule 470 or other portion of the rotatable locking element 458 can engage the lead 403 within the lead channel 460. The engagement and friction may lock the lead 403 within the lead anchor 450 so that the lead anchor 450 cannot slide along the lead 403. The lead anchor 450 is also attached to tissue within the patient's body so that the lead 402 is firmly held in place.

Figure 6:
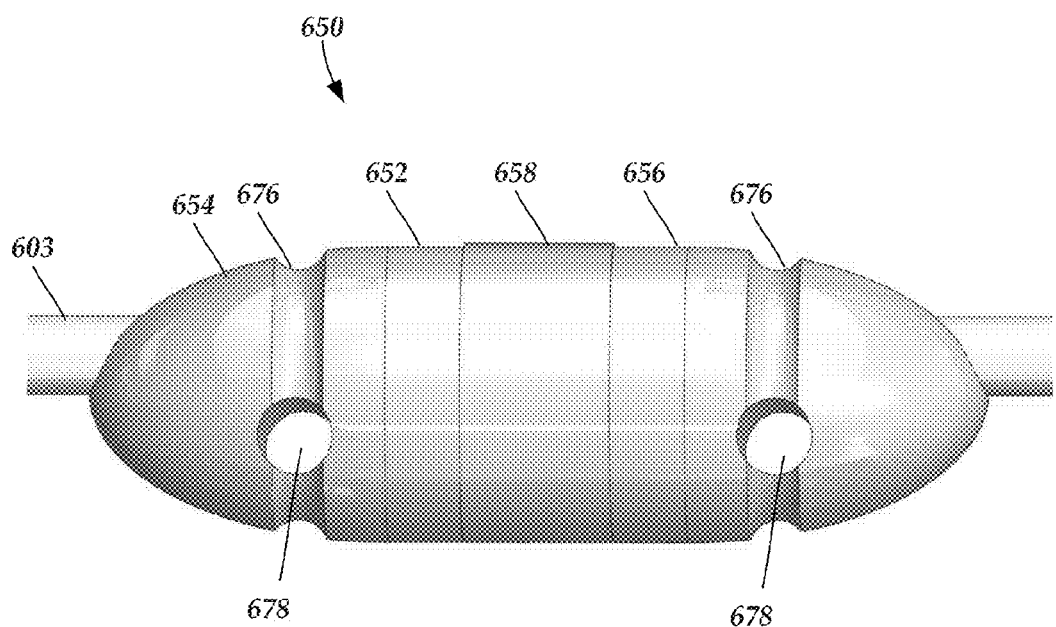
FIG. 6 is a schematic perspective view of another embodiment of a lead anchor, according to the invention.

FIG. 6A illustrates another embodiment of a lead anchor 650 that includes an anchor body 652 having a first portion 654 and a second portion 656, and a rotatable locking element 658, all of which can be similar in function and structure to the corresponding elements of the lead anchor 450 of FIGS. 4A-4C. As shown, the lead axis may be displaced from the primary axis of the lead anchor 650. In this embodiment, the anchor body 652 may defines one or more suture holes 678 (and optional suture grooves 676) through the anchor body 452 to allow a suture to pass through. The suture can be secured or tied to the surrounding tissue within the patient's body to ensure that the lead anchor 650 is fixed at a particular location or position.

Figures 7A, 7B, 7C:
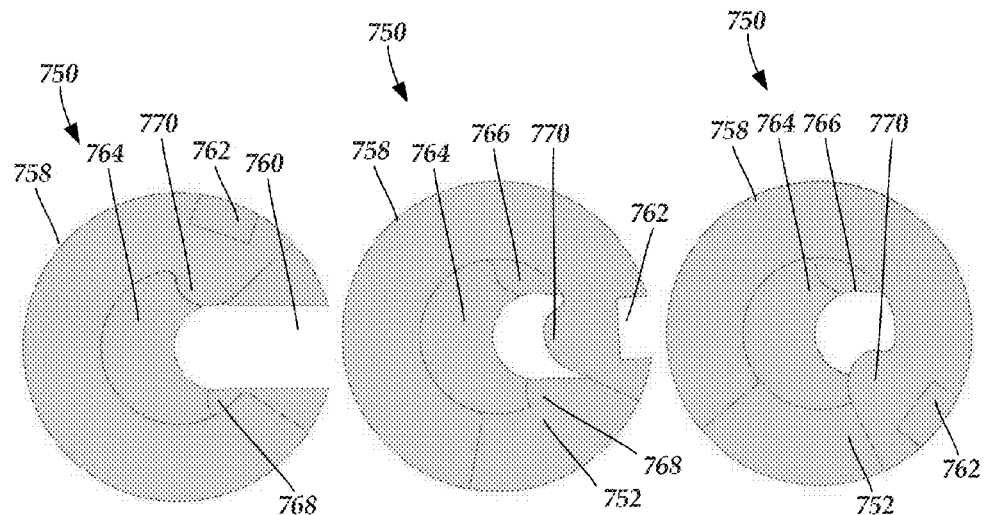
FIG. 7A is a schematic cross-sectional view of a lead anchor in the open position, according to the invention.
FIG. 7B is a schematic cross-sectional view of the lead anchor of FIG. 7A in an intermediate position, according to the invention.
FIG. 7C is a schematic cross-sectional view of the lead anchor of FIG. 7A in the closed position, according to the invention.

FIGS. 7A-7C illustrate, in cross-section, different positions of a rotatable locking element 758 relative to an anchor body 752 of a lead anchor 750 to demonstrate the opening and closing of the lead anchor. FIG. 7A is a schematic cross-sectional view of the lead anchor 750 in an open position. The lead anchor 750 may be similar in structure and function to the lead anchor 450 of FIGS. 4A-4C. The lead anchor body 752 has an axle 764 around which the rotatable locking element 758 is rotated. The anchor body 752 includes a channel lead 760 in which the lead can be received. The rotatable locking element 758 may include an indentation 762 or finger grip portion formed in an outer surface of the anchor body 752 to facilitate rotation of the locking element 758 by a user.

The axle 764, in the illustrated embodiment, also include a first end stop 766 and a second end stop 768, that each interact with a nodule 770 on the rotatable locking element 758 to prevent further rotation of the rotatable locking element 758 in one direction. In the illustrated embodiment, the first end stop 766 interacts with the nodule 770 on the locking element 758 to resist further rotation of the rotatable locking element 758 in a counterclockwise direction. Similarly, the second end stop 768 may be configured and arranged to interact with the nodule 770 on the locking element to resist further rotation of the rotatable locking element 758 in a clockwise direction.

FIG. 7B illustrates the lead anchor 750 in an intermediate position. The rotatable locking element 758 may be configured to transit from the open position to a closed position when rotated in a clockwise direction. FIG. 7C illustrates the lead anchor 750 in the closed position.

Figures 8A, 8B, 8C:
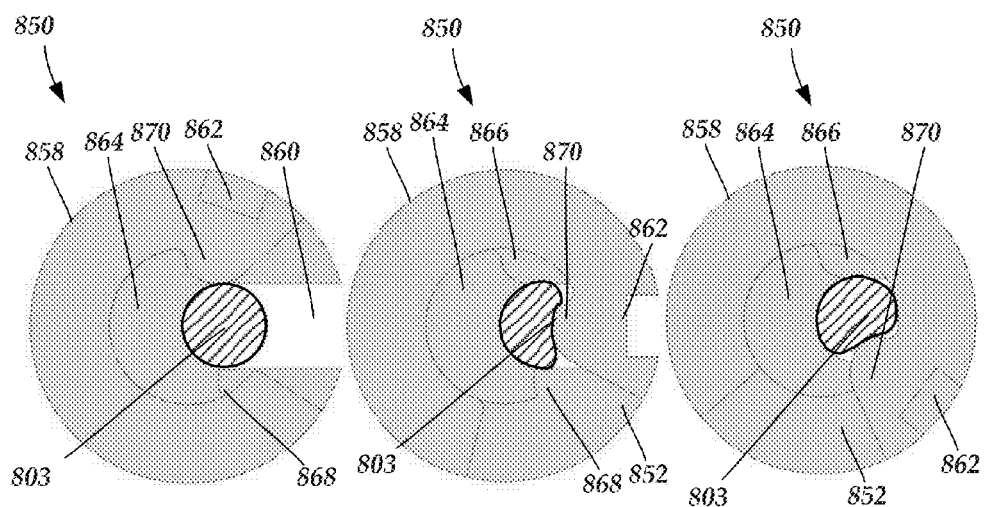
FIG. 8A is a schematic cross-sectional view of a lead anchor in the open position and a lead received in the lead anchor, according to the invention.
FIG. 8B is a schematic cross-sectional view of the lead and lead anchor of FIG. 8A in an intermediate position, according to the invention.
FIG. 8C is a schematic cross-sectional view of the lead and lead anchor of FIG. 8A in the closed position, according to the invention.

FIGS. 8A-8C are similar to FIGS. 7A-7C, but illustrate the position and arrangement of the lead in the lead anchor 850 during transition from open position to the closed position. FIG. 8A illustrates the lead anchor 850 in the open position and a lead 803 received in the lead anchor 850. As shown, a portion of the lead 803 is inserted into an open lead channel 860 of the lead anchor 850 with a rotatable locking element 858 in an open position. There can be clinical advantages to the anchor 850 that may be side loaded. For example, the speed at which the lead 803 can be attached to the anchor can be increased, and the ease of alignment between the anchor 850 and the lead 803 can be enhanced and the overall profile of the anchor 850 can be reduced.

The locking element 858 can be rotated to a closed position to lock the lead 803 within the lead anchor 850 by user engagement of an indentation 862 in an outer surface of the locking element 858. Further, the locking element 858 may be rotated from the open position to the closed position around a center of rotation of the locking element 858 that is offset from a central longitudinal axis of the lead 803 inserted in the lead channel 860.

FIG. 8B illustrates the lead and lead anchor 850 in an intermediate position. As the locking element 858 is closed, the anchor 850 preferably engages the lead 803 reaching a point of maximum engagement prior to the closed position. After this point of maximum engagement, further rotation of the locking element 858 results in reduced engagement of the lead 803. The lead's resistance to compression may promote further rotation, thereby urging the locking element 858 into the closed position. In at least some embodiments, the engagement of the lead arises, at least in part, because the physical center of the lead 803, when it is received in the lead channel, is laterally offset from the center of rotation of the rotatable locking element 858.

FIG. 8C illustrates the lead 803 and lead anchor 858 in the closed position. In the closed position, the nodule 870 of the locking element 858 engages the lead 803. In this particular embodiment, there is resistance to the rotation of the locking element 858 towards the open position because this would require additional compression of the lead, as describe above. Further, in the closed position, the entrance slit of the locking element is aligned with the lead channel 860 so as to prevent the lead 803 disposed in the lead channel 860 from disengaging from the lead anchor 850. During the rotation of the locking element 858, the nodule 870 engages a portion of the lead 803 disposed in the lead channel 860 to urge the locking element 858 to remain in the closed position and to securely lock the lead with respect to the lead anchor 850 to provide a resulting structure that is easy to manipulate and secure within a patient.

Unlocking the anchor 850 may require further engagement of the lead 803, which could provide a tactile signal to a practitioner when force is being applied to cause the locking element 858 to open. Thus, the lead 803 may remain stable and secured when the locking element 858 is in the closed or locked position and when no rotational force is input to the locking element 858.

A kit can be provided that includes a lead and one or more of the lead anchors described above. The kit may also include a control module coupleable to the lead.

One embodiment of a method of implanting a lead includes inserting a portion of a lead into an open lead channel of one of the lead anchors describe above with the rotatable locking element of the lead anchor in an open position. The locking element of the lead anchor is rotated to a closed position to lock the lead within the lead anchor. In the closed position, the nodule on the locking element may engage the lead and resist rotation of the locking element to the open position to prevent the lead disposed in the lead channel from disengaging from the lead anchor.

The lead is implanted into patient tissue and the lead anchor is attached to the tissue using any suitable attachment mechanism, such as, for example, at least one suture, staple, adhesive, or any other attachment device or material. The method may also include coupling a control module to the lead and implanting the control module into the tissue of the patient.

Figure 9:
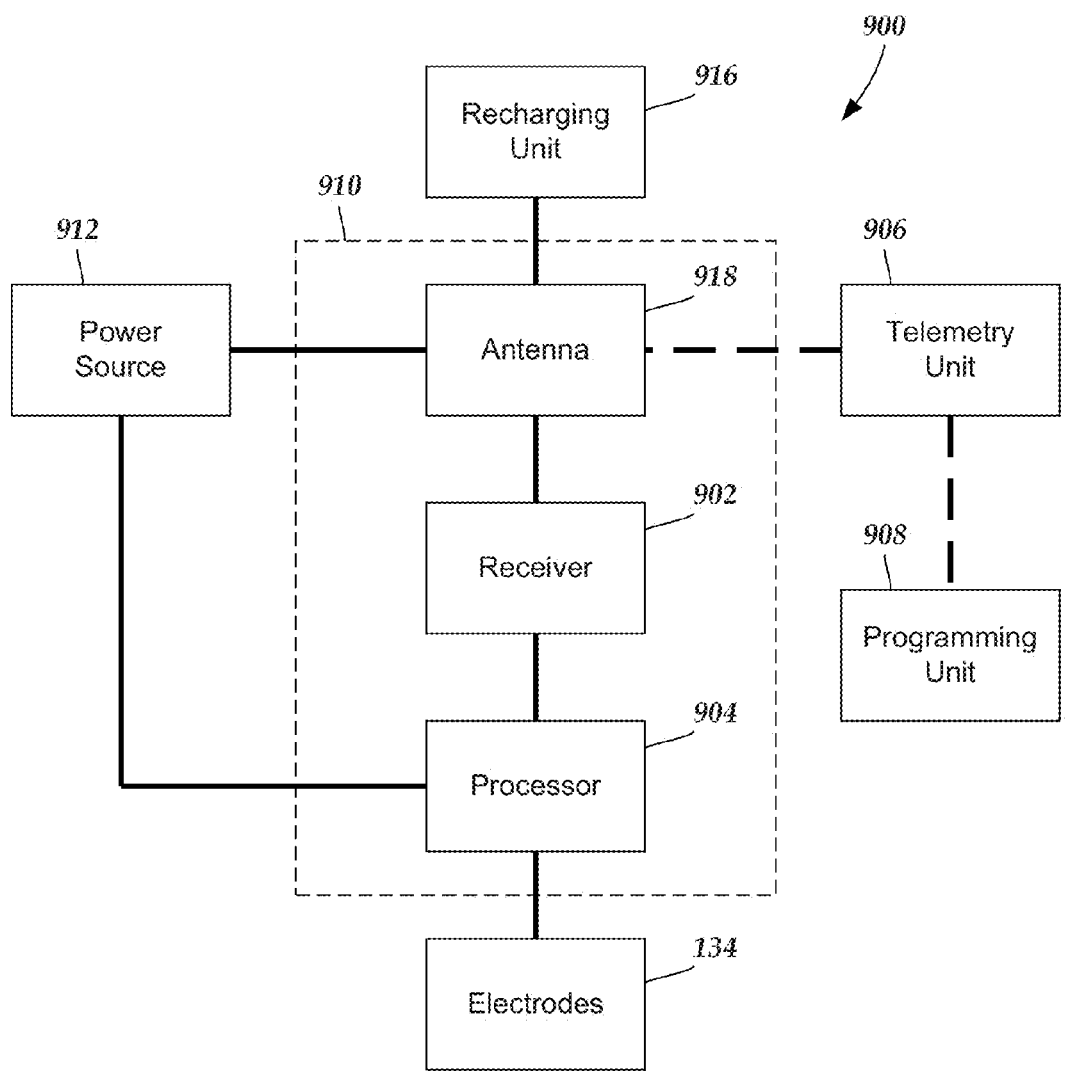
FIG. 9 is a schematic overview of one embodiment of components of a stimulation system, including an electronic subassembly disposed within a control module, according to the invention.

FIG. 9 is a schematic overview of one embodiment of components of an electrical stimulation system 900 including an electronic subassembly 910 disposed within a control module. It will be understood that the electrical stimulation system can include more, fewer, or different components and can have a variety of different configurations including those configurations disclosed in the stimulator references cited herein.

Some of the components (for example, a power source 912, an antenna 918, a receiver 902, and a processor 904) of the electrical stimulation system can be positioned on one or more circuit boards or similar carriers within a sealed housing of an implantable pulse generator, if desired. Any power source 912 can be used including, for example, a battery such as a primary battery or a rechargeable battery. Examples of other power sources include super capacitors, nuclear or atomic batteries, mechanical resonators, infrared collectors, thermally-powered energy sources, flexural powered energy sources, bioenergy power sources, fuel cells, bioelectric cells, osmotic pressure pumps, and the like including the power sources described in U.S. Pat. No. 7,437,193, incorporated herein by reference.

As another alternative, power can be supplied by an external power source through inductive coupling via the optional antenna 918 or a secondary antenna. The external power source can be in a device that is mounted on the skin of the user or in a unit that is provided near the user on a permanent or periodic basis.

If the power source 912 is a rechargeable battery, the battery may be recharged using the optional antenna 918, if desired. Power can be provided to the battery for recharging by inductively coupling the battery through the antenna to a recharging unit 916 external to the user. Examples of such arrangements can be found in the references identified above.

In one embodiment, electrical current is emitted by the electrodes 134 on the paddle or lead body to stimulate nerve fibers, muscle fibers, or other body tissues near the electrical stimulation system. The processor 904 is generally included to control the timing and electrical characteristics of the electrical stimulation system. For example, the processor 904 can, if desired, control one or more of the timing, frequency, strength, duration, and waveform of the pulses. In addition, the processor 904 can select which electrodes can be used to provide stimulation, if desired. In some embodiments, the processor 904 selects which electrode(s) are cathodes and which electrode(s) are anodes. In some embodiments, the processor 904 is used to identify which electrodes provide the most useful stimulation of the desired tissue.

Any processor can be used and can be as simple as an electronic device that, for example, produces pulses at a regular interval or the processor can be capable of receiving and interpreting instructions from an external programming unit 908 that, for example, allows modification of pulse characteristics. In the illustrated embodiment, the processor 904 is coupled to a receiver 902 which, in turn, is coupled to the optional antenna 918. This allows the processor 904 to receive instructions from an external source to, for example, direct the pulse characteristics and the selection of electrodes, if desired.

In one embodiment, the antenna 918 is capable of receiving signals (e.g., RF signals) from an external telemetry unit 906 which is programmed by the programming unit 908. The programming unit 908 can be external to, or part of, the telemetry unit 906. The telemetry unit 906 can be a device that is worn on the skin of the user or can be carried by the user and can have a form similar to a pager, cellular phone, or remote control, if desired. As another alternative, the telemetry unit 906 may not be worn or carried by the user but may only be available at a home station or at a clinician's office. The programming unit 908 can be any unit that can provide information to the telemetry unit 906 for transmission to the electrical stimulation system 900. The programming unit 908 can be part of the telemetry unit 906 or can provide signals or information to the telemetry unit 906 via a wireless or wired connection. One example of a suitable programming unit is a computer operated by the user or clinician to send signals to the telemetry unit 906.

The signals sent to the processor 904 via the antenna 918 and the receiver 902 can be used to modify or otherwise direct the operation of the electrical stimulation system. For example, the signals may be used to modify the pulses of the electrical stimulation system such as modifying one or more of pulse duration, pulse frequency, pulse waveform, and pulse strength. The signals may also direct the electrical stimulation system 900 to cease operation, to start operation, to start charging the battery, or to stop charging the battery. In other embodiments, the stimulation system does not include the antenna 918 or receiver 902 and the processor 904 operates as programmed.

Optionally, the electrical stimulation system 900 may include a transmitter (not shown) coupled to the processor 904 and the antenna 918 for transmitting signals back to the telemetry unit 906 or another unit capable of receiving the signals. For example, the electrical stimulation system 900 may transmit signals indicating whether the electrical stimulation system 900 is operating properly or not or indicating when the battery needs to be charged or the level of charge remaining in the battery. The processor 904 may also be capable of transmitting information about the pulse characteristics so that a user or clinician can determine or verify the characteristics.

The above specification, examples and data provide a description of the manufacture and use of the composition of the invention. Since many embodiments of the invention can be made without departing from the spirit and scope of the invention, the invention also resides in the claims hereinafter appended.

What is claimed as new and desired to be protected by Letters Patent of the United States is:

1. A lead anchor, comprising:
    an anchor body having a longitudinal axis, a circumference around the longitudinal axis, a longitudinal length, an exterior surface, a proximal end, and a distal end, the anchor body defining an open lead channel extending longitudinally, parallel to the longitudinal axis, from the proximal end to the distal end and open at the exterior surface of the anchor body along the longitudinal length of the anchor body from the proximal end to the distal end to permit lateral loading of a lead into the lead channel; and
    a rotatable locking element shaped as a portion of a ring and defining a central cavity and an entrance slit, the locking element further defining a protruding nodule extending into the central cavity,
    wherein the anchor body further defines a locking element channel arranged perpendicular to the lead channel and configured and arranged to receive the rotatable locking element and to permit rotation of the locking element circumferentially around the longitudinal axis of the anchor body from an open position to a closed position, wherein, in the open position, the entrance slit of the locking element is aligned with the lead channel of the anchor body so that a lead can be loaded into the lead channel and, in the closed position, the entrance slit is not aligned with the lead channel to prevent a lead disposed in the lead channel from disengaging from the lead anchor, wherein, when a lead is in the lead channel and the locking element is in the closed position, the nodule on the locking element engages the lead and resists rotation of the locking element to the open position.

2. The lead anchor of claim 1, wherein the anchor body comprises a first portion, a second portion, and an axle coupling the first portion to the second portion, wherein the rotatable locking element is disposed between the first and second portions and around the axle.

3. The lead anchor of claim 2, wherein the axle defines at least one end stop, each end stop being configured and arranged to interact with the nodule to prevent further rotation of the locking element in one direction.

4. The lead anchor of claim 1, wherein the locking element has an indentation formed in an outer surface thereof to facilitate rotation of the locking element by a user.

5. The lead anchor of claim 1, wherein the anchor body has a first end stop configured and arranged to interact with the nodule on the locking element to resist further rotation of the locking element in a clockwise direction around the longitudinal axis of the anchor body.

6. The lead anchor of claim 5, wherein the anchor body has a second end stop configured and arranged to interact with the nodule on the locking element to resist further rotation of the locking element in a counterclockwise direction around the longitudinal axis of the anchor body.

7. The lead anchor of claim 1, wherein the lead anchor comprises at least one suture channel formed in an outer surface of the anchor body.

8. The lead anchor of claim 1, wherein the anchor body defines one or more suture holes through the anchor body.

9. The lead anchor of claim 1, wherein the anchor body and locking element are arranged so that a center of rotation of the locking element is offset from a center of a lead received within the lead channel.

10. The lead anchor of claim 1, wherein the lead anchor is configured and arranged to engage a portion of the lead disposed in the lead channel using the nodule of the locking element when the locking element is rotated between the open and closed positions.

11. A kit, comprising:
    a lead; and
    the lead anchor of claim 1 configured and arranged for receiving the lead in the lead channel of the lead anchor.

12. The kit of claim 11, further comprising a control module coupleable to the lead.

13. A method of implanting a lead, the method comprising:
    inserting a portion of a lead into the open lead channel of the anchor body of the lead anchor of claim 1 with the rotatable locking element of the lead anchor in an open position, wherein, in the open position, the entrance slit of the locking element is aligned with the lead channel of the anchor body so that the lead can be inserted into lead channel; and rotating the locking element of the lead anchor circumferentially around the longitudinal axis of the anchor body of the lead anchor to the closed position to lock the lead within the lead anchor, wherein, in the closed position, the nodule on the locking element engages the lead and resists rotation of the locking element to the open position and the entrance slit of the locking element is not aligned with the lead channel to prevent the lead disposed in the lead channel from disengaging from the lead anchor.

14. The method of claim 13, further comprising implanting a distal portion of the lead into patient tissue, the distal portion of the lead comprising a plurality of electrodes disposed thereon.

15. The method of claim 13, further comprising attaching the lead anchor, with the portion of the lead inserted into the lead channel, to tissue using at least one suture.

16. The method of claim 13, wherein rotating the locking element comprises rotating the locking element from the open position to the closed position, wherein during the rotation the nodule of the locking element engages a portion of the lead disposed in the lead channel.

17. The method of claim 16, wherein, in the closed position, the nodule of the locking element engages a portion of the lead disposed in the lead channel.

18. The method of claim 13, wherein rotating the locking element comprises rotating the locking element from the open position to the closed position by user engagement of an indentation in an outer surface of the locking element.

19. The method of claim 13, wherein rotating the locking element comprises rotating the locking element from the open position to the closed position around a center of rotation of the locking element that is offset from a center of the lead inserted in the lead channel.

20. The method of claim 13, further comprising coupling a control module to the lead and implanting the control module.

\* \* \* \* \*